United States Patent
Ujvari (10) Patent No.: US 10,265,084 B2
(45) Date of Patent: *Apr. 23, 2019

(54) PERFORATOR

(71) Applicant: Mihaly Gyula Ujvari, Debrecen (HU)

(72) Inventor: Mihaly Gyula Ujvari, Debrecen (HU)

( * ) Notice: Subject to any disclaimer, the term of this patent is extended or adjusted under 35 U.S.C. 154(b) by 270 days.

This patent is subject to a terminal disclaimer.

(21) Appl. No.: 15/301,054

(22) PCT Filed: Mar. 30, 2015

(86) PCT No.: PCT/HU2015/000030
§ 371 (c)(1),
(2) Date: Sep. 30, 2016

(87) PCT Pub. No.: WO2015/150844
PCT Pub. Date: Oct. 8, 2015

(65) Prior Publication Data
US 2017/0027594 A1 Feb. 2, 2017

(30) Foreign Application Priority Data
Mar. 31, 2014 (HU) ..................................... 1400179

(51) Int. Cl.
*A61B 17/16* (2006.01)
*A61B 90/00* (2016.01)

(52) U.S. Cl.
CPC ...... *A61B 17/1695* (2013.01); *A61B 17/1617* (2013.01); *A61B 90/03* (2016.02); *A61B 2090/034* (2016.02)

(58) Field of Classification Search
CPC ............ A61B 17/1615; A61B 17/1617; A61B 17/162; A61B 17/1622; A61B 17/1624; A61B 17/1637; A61B 17/1642; A61B 17/1695
See application file for complete search history.

(56) References Cited

U.S. PATENT DOCUMENTS

| 4,362,161 | A  | * | 12/1982 | Reimels  | A61B 17/1695 |
|           |    |   |         |          | 606/173      |
| 5,330,480 | A  | * | 7/1994  | Meloul   | A61B 17/1617 |
|           |    |   |         |          | 606/170      |
| 2002/0050463 | A1 | * | 5/2002 | McDowell | A61B 17/0642 |
|           |    |   |         |          | 206/370      |
| 2009/0024129 | A1 | * | 1/2009 | Gordon  | A61B 17/1617 |
|           |    |   |         |          | 606/80       |
| 2013/0171585 | A1 | * | 7/2013 | Huang   | A61C 8/0092  |
|           |    |   |         |          | 433/173      |

* cited by examiner

*Primary Examiner* — Matthew J Lawson
*Assistant Examiner* — Amy R Sipp
(74) *Attorney, Agent, or Firm* — Olson & Cepuritis, Ltd.

(57) ABSTRACT

Perforator for drilling bone tissue, comprising a drive shaft (12) with rotation axis (t), a drill head (14) with the same rotation axis (t), a chipping head (16) arranged coaxially around the later. A first connecting profile (20) is provided on a proximal end (18) of the drill head (14), and a second connecting profile (24) is provided on a distal end (22) of the drive shaft (12) for cooperating with the first connecting profile (20) in order to transfer rotational movement of the drive shaft (12) to the drill head (14), and the drill head (14) and the chipping head (16) being connected to each other displaceably along the rotation axis (t).

12 Claims, 8 Drawing Sheets

PERFORATOR

CROSS-REFERENCE TO RELATED APPLICATIONS

This application is a U.S. National Stage of PCT/HU2015/000030, filed Mar. 30, 2015, which claims priority of Hungarian Patent Application No. P1400179, filed Mar. 31, 2014, each of which is incorporated herein by reference.

The present invention relates to a perforator for perforating bone tissue, which perforator comprises a drive shaft having a rotation axis, a drill head which is coaxial with the rotation axis, and a chipping head arranged coaxially around the drill head.

The perforator is a medical device which can be used to perform trepanation on the crane i.e. drill a hole therein, and in particular to perform craniotomy after the trepanation. During the trepanation of the crane it is a problem, that substantial pressure has to be applied for advancing the drill head, however, the advancing of the drill head needs to be stopped immediately after perforation of the bone in order to prevent the drill head from penetrating and damaging the dura mater. In order to carry out surgical closure successfully it is a prerequisite that the dura mater must stay undamaged to be able to create fluid (liquor) sealing seam thereon.

A further problem is that the bone tissue of the crane is not a homogenous structure. The crane typically comprises a more dense outer and inner bone plate and a looser, porous inner soft bone layer therebetween, the so-called spongiosa. When designing the structure of the perforator it must be ensured that the quality and performance of the drilling stays the same within the different tissue structures, while at the same time the drilling process must be interrupted as soon as the inner bone plate is penetrated (drilled through) which is rather thin as compared to the other tissue structures lying thereover, in order to protect the dura tissue right underneath of the inner bone structure as explained above. The cutting edge should be designed such that when the inner bone plate is penetrated a disk like formation remains, which further protects the dura tissue.

This problem is solved by the perforator according to U.S. Pat. No. 4,456,010 patent in such a way that the drill head is surrounded by a coaxial chipping head and the two are connected by a bolt pin, which extends through the drill head and terminates in a triangular opening formed in the wall of the chipping head, whereby the relative displacement of the drill head and the chipping head is limited by the triangular opening. The drive shaft of the perforator is formed as a Hudson stem having a distal end with a groove for receiving the portion of the bolt pin that is between the drill head and the chipping head. One of the vertices of the triangle shaped opening is in a proximal position, whereby if the drill head is pressed against the cranial bone the drill head, as a result of the counter pressure, is displaced in the proximal direction and the bolt pin advances into the proximal vertex and into the groove of the Hudson stem, provided it is lying in the appropriate direction, which stem then rotates both the drill head and the chipping head via the bolt pin. The drill head extends beyond the chipping head, whereby the drill head is the first to penetrate through the cranial bone. When this happens, the counter force acting on the drill head is reduced drastically, thus the rotational speed of the drill head increases with respect to the chipping head. Consequently, the end of the bolt pin advances such that it is guided by the edge of the triangular opening in the chipping head whereby the drill head is displaced in the distal direction with respect to the bolt pin. This displacement is further facilitated by a biased spring. As a result of the distal displacement the bolt pin extending through the drill head is released from the groove of the drive stem, thus the driving torque acting on the drill head and the chipping head ceases and the bone tissue stops the chipping head rotating therein and together with it the drill head.

The disadvantage of this solution is that if during the operation the advancing of the perforator has to be interrupted for any reason or if the counter force acting on the drill head decreases due to a change in the tissue quality then the above described mechanism may lead to the disengagement of the drive stem after which it is difficult to find the bolt pin with the groove of the drive stem and reengage the two. It is practically always a problem that when reaching the spongiosa between the outer and the inner bone plates the drill head may stop too early without perforating the spongiosa and the inner bone plate.

It is an object of the present invention to overcome the problems associated with the prior art.

These objects are achieved by a perforator according to claim 1.

Further advantageous embodiments of the invention are defined in the attached dependent claims.

Further details of the invention will be explained by way of exemplary embodiments with reference to the figures.

Figure 1:
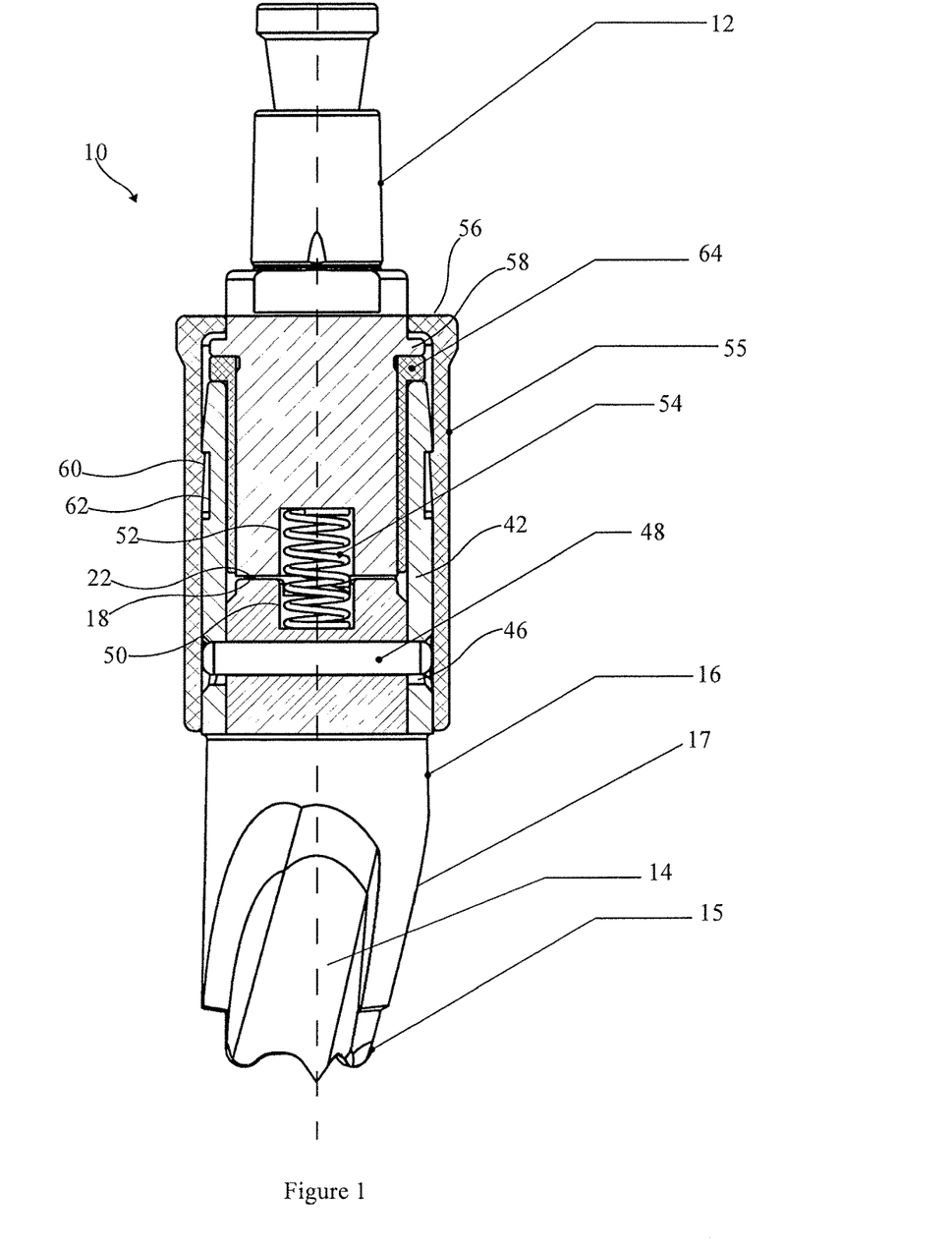
FIG. 1 is a partially cut-away side view of a perforator according to the invention.

FIG. 1 depicts a preferred embodiment of a perforator 10 according to the invention, which comprises a drive shaft 12 with rotation axis t, a drill head 14 having the same rotation axis t and a chipping head 16 arranged coaxially around the drill head 14. The drive shaft 12 may be connected to a revolution reducer, so-called TREAPAN adapter, coupled with a drive motor (not shown), and may be formed for example as a Hudson cone as better seen in FIGS. 2a and 2b. The drill head 14 and the chipping head 16 each comprise a distal cutting edge 15 and 17 respectively, and the distal cutting edge 15 of the drill head 14 extends beyond the distal cutting edge 17 of the chipping head 16.

Figure 2A:
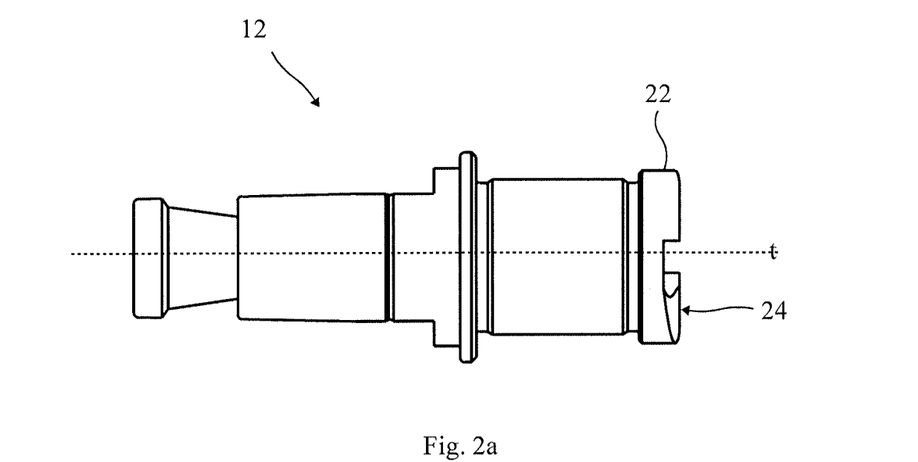
FIG. 2a is a side view of the drive shaft of the perforator according to FIG. 1.
Figure 2B:
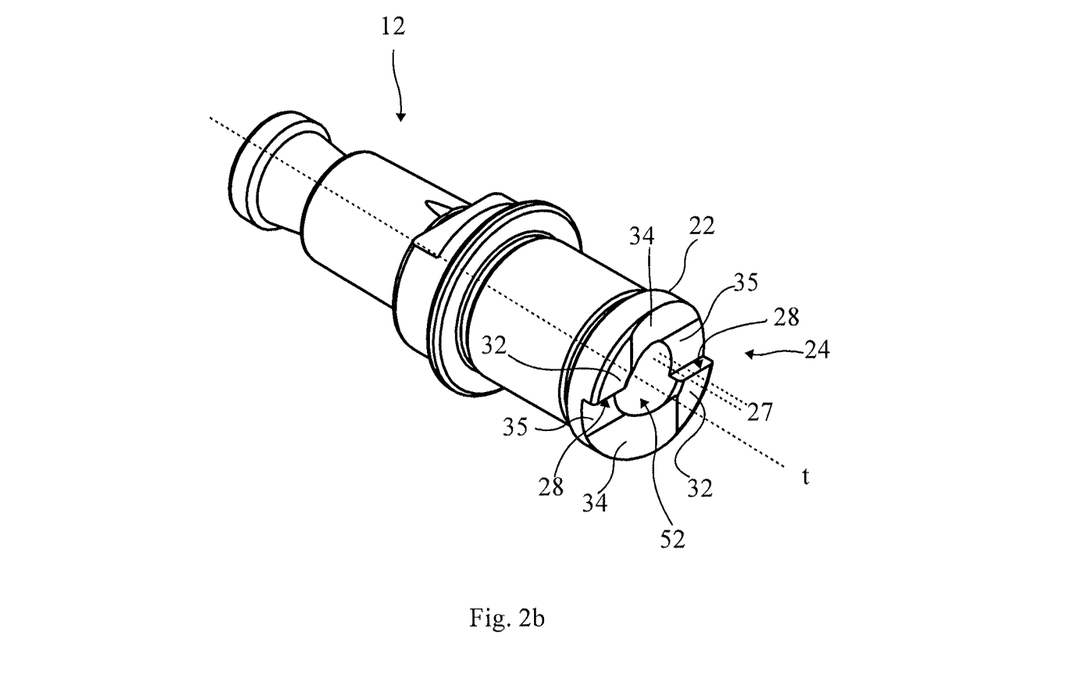
FIG. 2b is a perspective view of the drive shaft of the perforator according to FIG. 1.

A first connecting profile 20 is provided on a proximal end 18 of the drill head 14 (see FIGS. 3a, 3b), while a second connecting profile 24 is provided on a distal end 22 of the drive shaft 12 (see FIGS. 2a, 2b). The drill head 14 is arranged so as to be displaceable along the rotation axis t with respect to the chipping head 16 (and with respect to the drive shaft 12 at the same time) between a proximal position (see FIG. 5a) and a distal position (see FIG. 5b). In the proximal position the second connecting profile 24 on the distal end 22 of the drive shaft 12 engages the first connecting profile 20 and cooperates therewith such as to transmit rotational motion from the drive shaft 12 to the drill head 14. In the distal position the first connecting profile 20 on the proximal end 18 of the drill head 14 and the second connecting profile 24 on the distal end 22 of the drive shaft 12 are disengaged, whereby the driving torque ceases as will be explained later on.

Figure 3A:
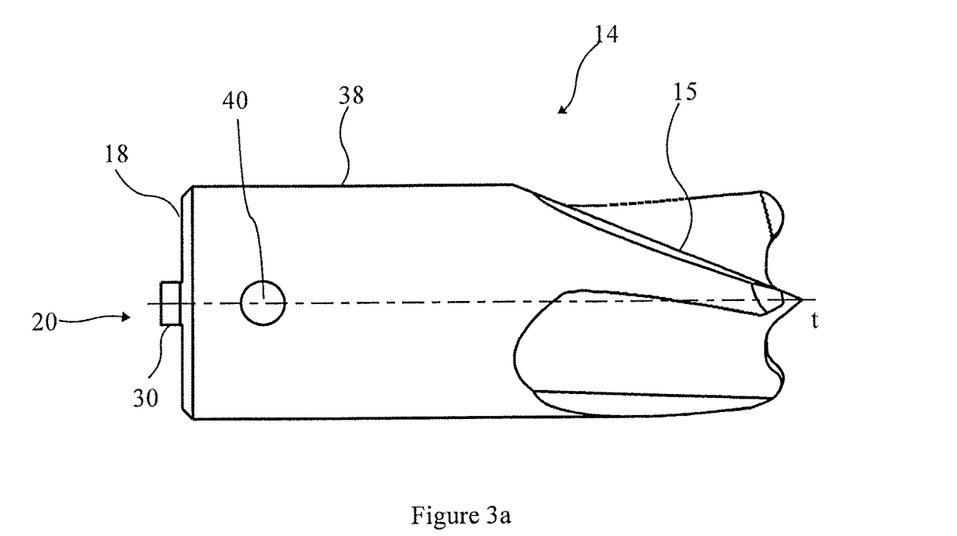
FIG. 3a is a side view of the drill head of the perforator according to FIG. 1.
Figure 3B:
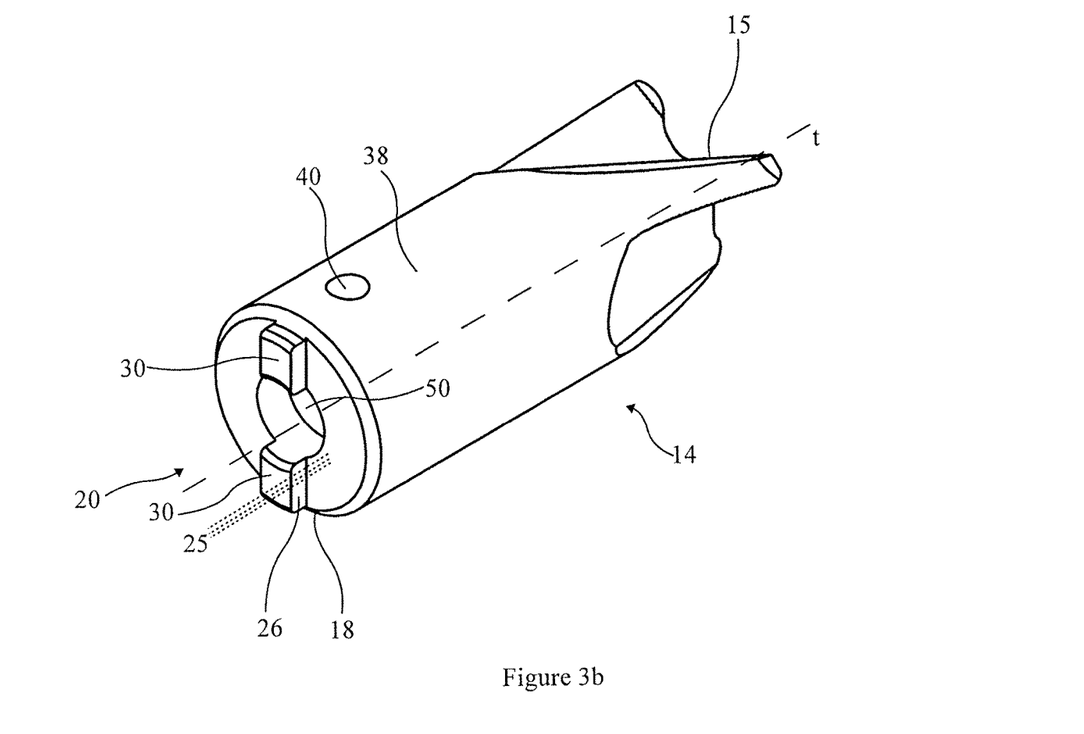
FIG. 3b is a perspective view of the drill head of the perforator according to FIG. 1.

The first connecting profile 20 formed on the drill head 14 comprises at least one, but according to the present embodiment two abutting surfaces 26 defined by generating lines 25 that are substantially parallel with the rotational axis t.

The second connecting profile 24 on the drive shaft 12 also comprises at least one driving surface 28 defined by generating lines 27 that are parallel with the rotational axis t. Preferably, the same number of driving surfaces 28 are provided as abutting surfaces 26.

Only a few exemplary generating lines 25 and 27 are depicted in FIGS. 2b and 3b respectively, and in the case of the present embodiment these define rectangular abutting surfaces 26 and driving surfaces 28 respectively. As will be explained in more detail later on the abutting surfaces 26 and the driving surfaces 28 need to satisfy basically two requirements: they must allow transmission of the rotational motion of the drive shaft 12 to the drill head 14 and they must allow relative displacement of the drive shaft 12 and the drill head 14 along the rotational axis t. Consequently, the abutting surface 26 and the drive surface 28 need not necessarily be planar surfaces, they can be for example curved surfaces complementing each other, for example wave-like surfaces. Continuousness of the surfaces is also not required, the surface may have interruptions, ribs, perforations, etc. Furthermore, the abutting surface 26 and the drive surface need not lie in a radial direction and may still be able to transmit rotational motion.

According to the present invention the two abutting surfaces 26 and the two driving surfaces 28 each delimit a projection 30 and 32, which projections 30, 32 project in the direction of the rotational axis t. The projections 32 of the drive shaft 12 are formed with a wedge surface 34 on their side opposite the driving surface 28. The length of the wedge surfaces 34 is preferably such that a clearance 35 is provided between the wedge surface 34 and the neighbouring driving surface 28 for receiving the projections 30 of the first connecting profile 20 of the drill head 14. Naturally, an inverted design is also conceivable, wherein the projections 30 of the drill head 14 are formed with a wedge surface on their side opposite the abutting surface 26.

Preferably, the projections 30 of the first connecting profile 20 of the drill head 14 and the projections 32 of the second connecting profile 24 of the drive shaft 12 are formed rotation-symmetrically with respect to the rotational axis t (i.e. formed evenly spaced around the circumference of a circle), whereby the proximal end 18 of the drill head 14 may engage the distal end 22 of the drive shaft 12 in more than one position. Engagement is understood to describe the situation wherein the projections 30 of the drill head 14 are received in the clearances 35 of the drive shaft 12 and the abutting surfaces 26 and the driving surfaces 28 abut each other.

In case of the present embodiment the two projections 30 of the connecting profile 20 are rotated with respect to each other by 180 degrees around the rotational axis t, however this angle depends on the number of the projections 30. For example, in case of three projections 30, those are preferably evenly spaced along the circumference of the proximal end 18, being in positions rotated by 120 degrees with respect to each other. In case a number of n projections 30 are provided those are preferably rotated by 360/n degrees with respect to the neighbouring projection 30. The connecting profile 24 of the distal end 22 of the drive shaft 12 is designed to correspond to the number and arrangement of the abutting surfaces 26 and the projections 30; accordingly, the projections 32 of the drive shaft 12 are preferably also formed rotation-symmetrically and evenly spaced along the circumference of the distal end 22.

Figure 5A:
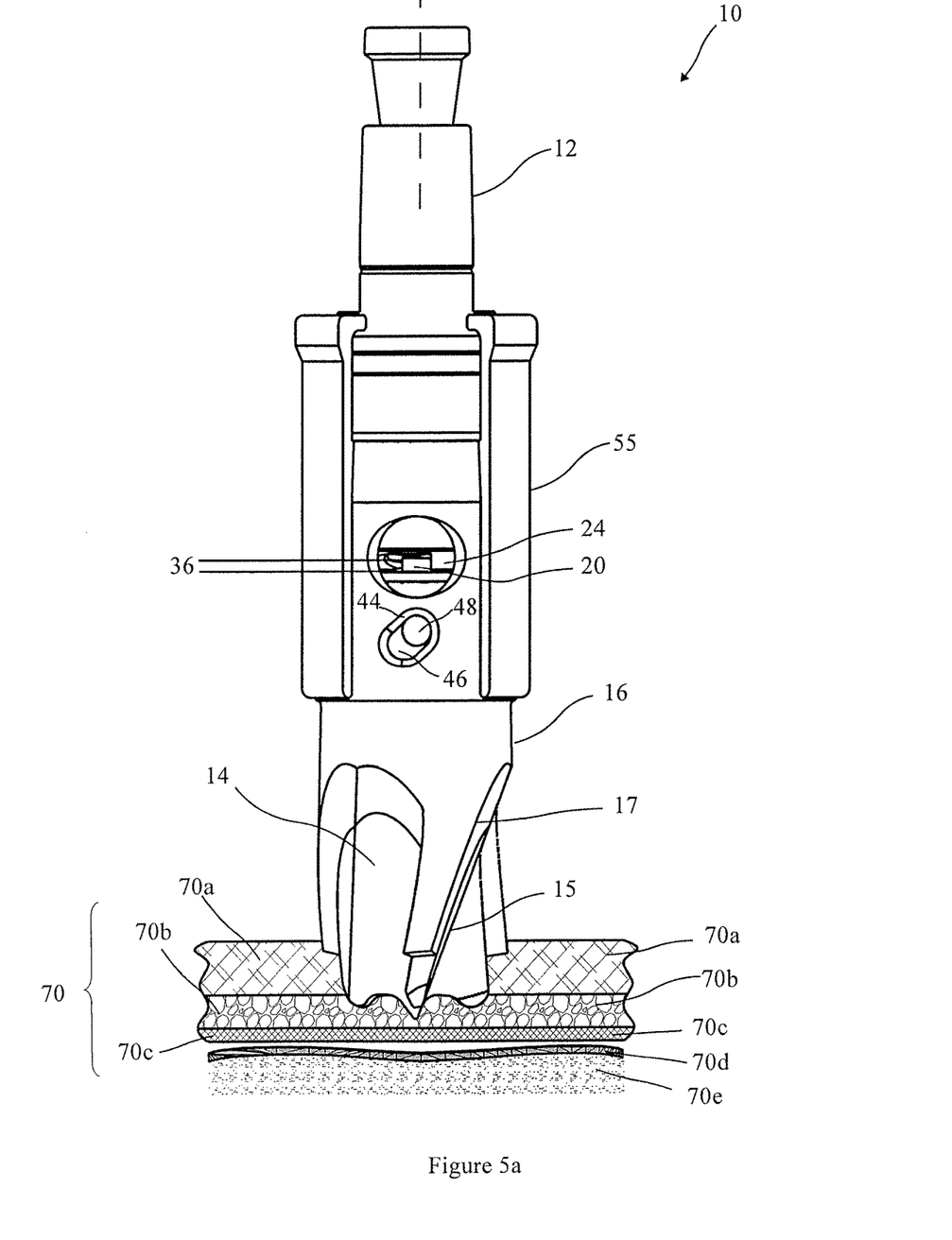
FIG. 5a is a partially cut-away side view of the perforator according to FIG. 1 in a drill position.

When the connecting profile 20 of the drill head 12 engages the connecting profile 24 of the drive shaft 14 the abutting surface 26 and the driving surface 28 abutting each other overlap in the direction of the rotational axis t and contact each other along a connection length 36 (see FIG. 5a). If the length of the abutting surface 26 and of the driving surface 28 is the same along the rotational axis t then the overlapping is complete, otherwise the shorter element determines the connection length 36. The connection length 36 determines the distance by which the proximal end 18 of the drill head 14 must be displaced from the distal end 22 of the drive shaft 12 in order to terminate the torque transmission connection between the two. Preferably, the connection length 36 (i.e. the length of the abutting surface 26 or the driving surface 28, which ever is shorter, measured along the rotational axis t) is between 0.4 to 1 mm, preferably 0.6 to 0.9 mm, more preferably approximately 0.7 mm. The drill head 14 may be displaced along the rotational axis t by a distance corresponding to the connection length 36 before the drive mechanism is disengaged.

Figure 4A:
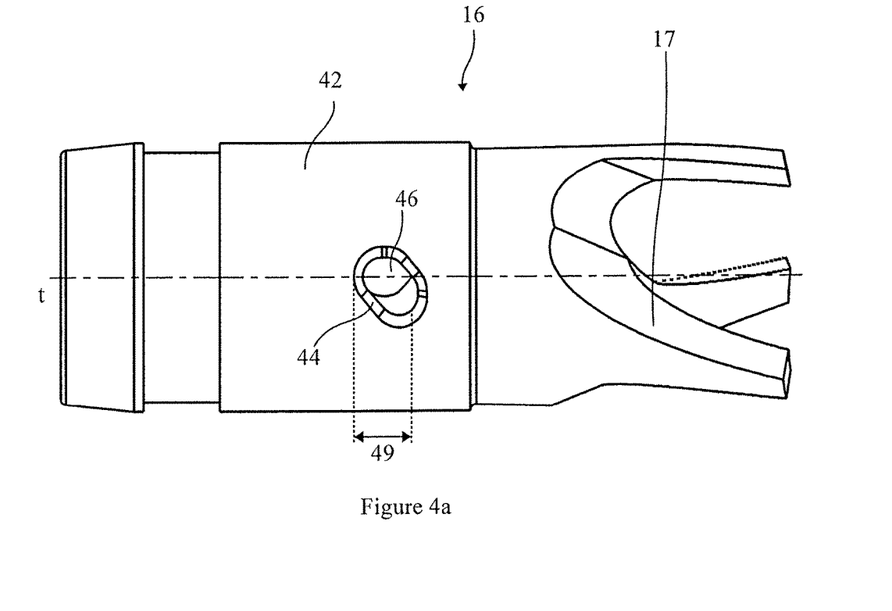
FIG. 4a is a side view of the chipping head of the perforator according to FIG. 1.
Figure 4B:
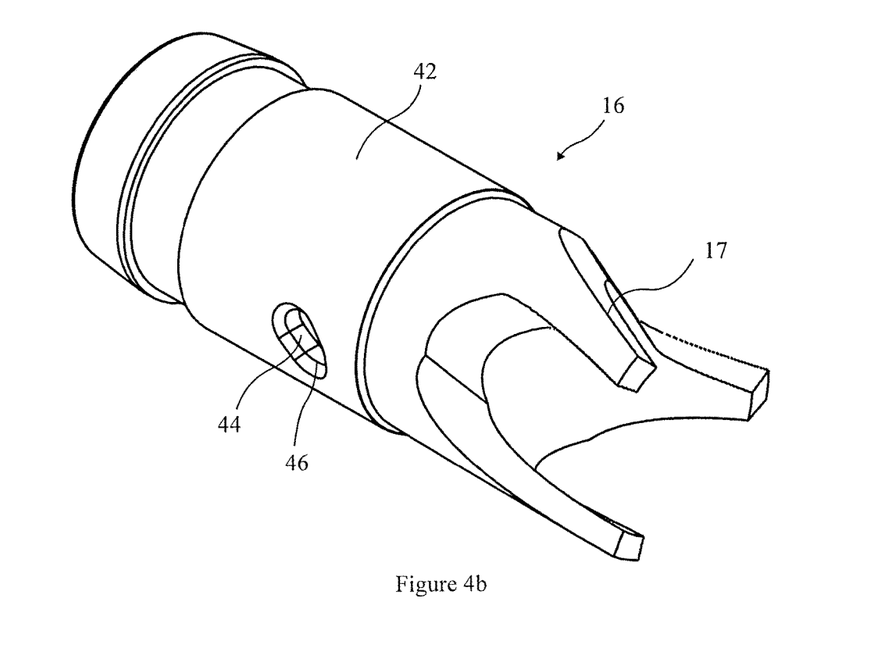
FIG. 4b is a perspective view of the chipping head of the perforator according to FIG. 1.

Disengagement of the drive mechanism can be ensured by providing a connection between the drill head 14 and the chipping head 16, which transforms relative rotation of the drill head 14 and the chipping head 16 around the rotational axis t into relative displacement along the rotational axis t. According to an exemplary embodiment this connection is ensured such that the drill head 14 comprises a bore hole 40 extending through an external surface 38 of the drill head 14, and an inwardly opening groove 46 with a proximal helical edge 44 corresponding to the driving direction is provided in a cylindrical wall 42 of the chipping head 16. An angle α between the helical edge 44 and the rotational axis t is preferably 40 to 50 degrees. In case of the embodiment depicted in FIGS. 4a and 4b this groove 46 is a helical groove formed through the wall 42, however, grooves 46 with other shapes may be applied as well, which have a suitable proximal helical edge 44, such as triangle shaped grooves 46. The connection between the drill head 14 and the chipping head 16 is ensured by a bolt pin 48 arranged in the bore hole 40 of the drill head 14 and extending into the groove 46 of the chipping head 16, which bolt pin 48 is guided by the proximal helical edge 44. The helical edge 44 is formed such that its elevation 49 is greater than the connection length 36 in order to provide for disengagement of the first connection profile 20 of the proximal end 18 of the drill head 14 from the second connection profile 24 of the of the distal end 22 of the drive shaft 12 such as to terminate the torque transmission connection between the two when the bolt pin 48 is guided to its distal position (see FIG. 5b) along the trajectory defined by the edge 44.

The perforator 10 is preferably provided with a mechanism for biasing the proximal end 18 of the drill head 14 from the distal end 22 of the drive shaft 12 when the perforator 10 is not being used. This can be achieved for example by providing nests 50 and 52 in the proximal end 18 of the drill head 14 and in the distal end 22 of the drive shaft 12 respectively, which nests 50, 52 open into one another when the drill head 14 and the drive shaft 12 are engaged and wherein a spring 54 is arranged. The spring 54 is compressed by the two nests 50, 52 along the rotational axis t when the drill head 14 and the drive shaft 12 are engaged, consequently, the spring 54 forces the drill head 14 into the distal position which is defined by the bolt pin 48 extending into the groove 46 of the chipping head 16 and traversing the bore hole 40 of the drill head 14.

The drive shaft 12 and the chipping head 16 is preferably arranged at a constant distance with respect to each other which is preferably ensured with a case 55 surrounding and connecting the drive shaft 12 and the chipping head 16. According to the present embodiment the case 55 is provided with a proximal flange 56 that abuts a collar 58 of the drive shaft 12 as illustrated in FIG. 1. In order to connect to the chipping head 16 the case 55 is provided with an internal circumferential shoulder 60, which engages an external circumferential groove 62 of the wall 42 of the chipping head 16. The case 55 is preferably made of plastic material or other deformable material such that when it is pulled over the assembled components from the direction of the drive shaft 12, the shoulder 60 is deformed and forced into the groove 62 of the chipping head 16 while the proximal flange 56 abuts the collar 58 of the drive shaft 12.

The wall 42 of the chipping head 16 preferably extends beyond the drill head 14 in the proximal direction and a slide ring 64 is arranged between the drive shaft 12 and the proximally extending wall 42. The slide ring 64 functions as a bearing and is preferably made of soft plastic material or similar material in order to prevent abrasion of the preferably metal drive shaft 12 and the wall 42 of the chipping head 16 during rotation.

Figure 5B:
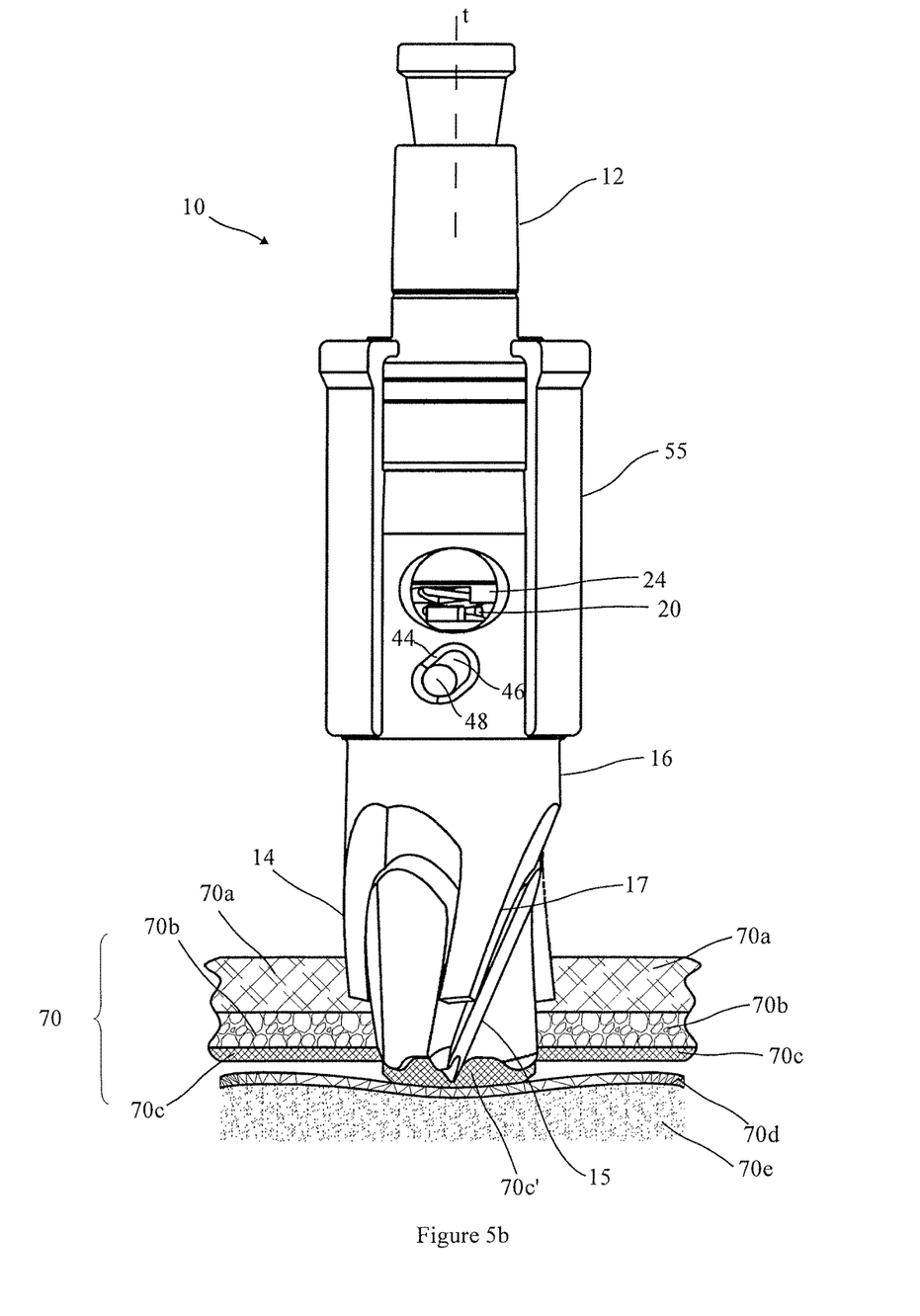
FIG. 5b is a partially cut-away side view of the perforator according to FIG. 1 in a disengaged position.

The use of the perforator 10 according to the invention will now be described with reference to FIGS. 5a and 5b.

The perforator 10 is used for drilling bone tissue 70, in particular cranial bone tissue. The bone tissue 70 comprises the following components following each other from the external side to the internal side: external bone plate 70a, spongiosa 70b (porous inner soft bone layer), internal bone plate 70c. This is followed by the dura tissue 70d, which must not be drilled through and which is bordering the inner brain water 70e.

Before starting the drilling the drive shaft 12 of the perforator 10 is fixed in a revolution reducing adapter coupled with a drill motor, then the distal cutting edge 15 of the drill head 14 is pressed against the bone tissue 70. As a result, the drill head 14 is displaced in the proximal direction with respect to the chipping head 16 along the rotational axis t until the bolt pin 48 extending through the drill head 14 reaches its proximal end position illustrated in FIG. 5a. During this displacement the spring 54 arranged within the nests 50 and 52 is compressed. In the fully compressed state, i.e. in the proximal position of the drill head 14, the abutting surfaces 26 of the first connecting profile 20 on the proximal end 18 of the drill head 14 and the driving surfaces 28 of the second connecting profile 24 on the distal end 22 of the drive shaft 12 abut each other along the whole of the connection length 36. When starting the drill motor, the drive shaft 12 starts to rotate and the driving surfaces 28 of its second connecting profile 24 exert drive torque on the abutting surfaces 26 of the first connecting profile 20 on the proximal end 18 of the drill head 14, as a result of which the drill head 12 starts to rotate around the rotational axis t, and therewith the chipping head 16 as well, which is connected with the drill head 12 by the bolt pin 48. By continuously pushing the perforator 10 in the distal direction of the bone tissue 70, first the distal cutting edge 15 of the rotating drill head 14, and then the distal cutting edge 17 of the co-rotating chipping head 16 start to cut into the bone tissue 70 and gradually advance therein.

In case of drilling a cranial bone, at the end of the drilling, when the distally extending cutting edge 15 of the drill head 14 has cut through the spongiosa 70b of the bone tissue 70 and starts to penetrate the internal bone plate 70c of the bone tissue 70, the counter force acting on the drill head 14 drastically decreases while the cutting edge 17 of the chipping head 16 lying in the distal direction is still inside the external bone structure 70a—or having drilled there through, it is still in the spongiosa 70b—requiring substantial driving torque to be rotated therein. The drill head 14 exerts torque on the chipping head 16 by way of the bolt pin 48. However, because the groove 46, which receives the bolt pin 48, has a helical proximal edge 44 in the direction of the rotation, hence the counter force acting on the bolt pin 48 comprises a force component which is parallel with the rotational axis t and is directed in the distal direction (i.e. in the direction of the bone tissue 70), which, in absence of a counter force exerted by the bone tissue 70, advances the drill head 14 in the distal direction (in the direction of the bone tissue 70) with respect to the chipping head 16 until the bolt pin 48 reaches its distal end position corresponding to the distal position of the drill head 14 as can be seen in FIG. 5b. In other words, the relative rotation of the drill head 14 and the chipping head 16 around the rotational axis t is transformed into relative displacement along the rotational axis t with the help of the helical edge 44 of the groove 46, which edge 44 is formed in the direction of the rotation, and with the help of the bolt pin 48, which is displaceable in the groove 46.

Since the case 55 holds the drive shaft 12 at a constant distance from the chipping head 16, thus the drill head 14 is not only displaced relative to the chipping head 16 but is also displaced relative the drive shaft 12. Consequently, the abutting surfaces 26 of the first connecting profile 20 of the drill head 14 are gradually shifted along the driving surfaces 28 of the second connecting profile 24 of the drive shaft 12. As long as the extent of shifting is less then the connection length 36, the drill head 14 is still driven by the drive shaft 12, accordingly, by suitable dimensioning of the connection length 36 it is possible to achieve that the drill head 14 cuts partially or wholly through the internal bone plate 70c while shifting in the distal direction. When the extent of the shifting exceeds the connection length 36, the abutting surfaces 26 of the first connecting profile 20 of the drill head 14 disengage the driving surfaces 28 of the second connecting profile 24 of the drive shaft 12, whereby the driving torque ceases to act on the drill head 14, and together with it, on the chipping head 16. In absence of a driving torque the chipping head 16 and the drill head 14 connected therewith by the bolt pin 48 come to a halt, whereby the perforator 10 only just cuts through the internal bone plate 70c of the bone tissue 70, and automatically stops thereafter, in order not to advance into the cranial space and not to damage the dura tissue 70d.

Releasing of the driving mechanism is further facilitated by the spring 14 which is arranged in the nests 50, 52 of the drive shaft 12 and of the drill head 14 respectively, opening into each other. The spring 14 also works to force the drill head 14 in its released state depicted in FIG. 5b. It is noted however, that in case of applying the groove 46 with the helical edge 44, this edge 44 is sufficient to force the bolt pin 48 and together with it the drill head 14 to advance in the distal direction, whereby release of the drive mechanism would be ensured without the presence of the spring 54 as well. It is further noted, that by applying a suitably designed spring 54 the release of the drive mechanism would occur even if the edge 44 were parallel with the rotational axis t, and even if the edge 44 were to run helically in the direction opposite the rotational direction. Accordingly, such embodiments are also conceivable wherein only relative displacement in the direction of the rotational axis t is allowed between the drill head 14 and the chipping head 16 and no relative rotation. However, preferably the two solutions are applied in combination in order to increase security, i.e. the groove 46 is formed with a helical edge 44 running in the rotational direction (e.g. as a linear groove), and a compressed spring 54 is disposed between the drive shaft 12 and the drill head 14.

The perforator 10 according to the invention has for advantage that the drive mechanism realised through the first and second connecting profiles 20, 24 is independent from the release mechanism, which can be realised for example by the above described groove 46 and bolt pin 48 which is displaceable therein and/or by the spring 54 disposed in the nests 50, 52. The advantage of this is that the drill head 14 does not disconnect from the drive shaft 12 as long as the distal displacement of the drill head 14 does not exceed the connection length 36. Consequently, if advancing of the perforator 10 should be stayed for any reason during the drilling process or if the counter force acting on the drill head 14 temporarily decreases due to a change in the tissue quality, this does not result straight away in decoupling of the drive mechanism. This also solves the problem of drilling through the thin bone plate 70c internally covering the bone tissue 70 of the crane, by appropriate choice of the connection length 36, the drill head 14 only just perforates the internal bone plate 70c creating a disk 70c' from its material in front of the drill head 14 before coming to a stop.

A further advantage of the perforator 10 according to the invention is that if the drive mechanism is disengaged—for example because the user is forced to temporarily pull back the perforator 10 for any reason—then if the drill head 14 is pressed against the bone tissue 70 again then the wedge surface 34 on the second connecting profile 24 automatically directs the projections 30 of the first connection profile 20 into the clearances 35, i.e. into the position wherein the abutting surfaces 26 abut the driving surfaces 28. This greatly facilitates re-coupling of the drive mechanism.

Figure 6A:
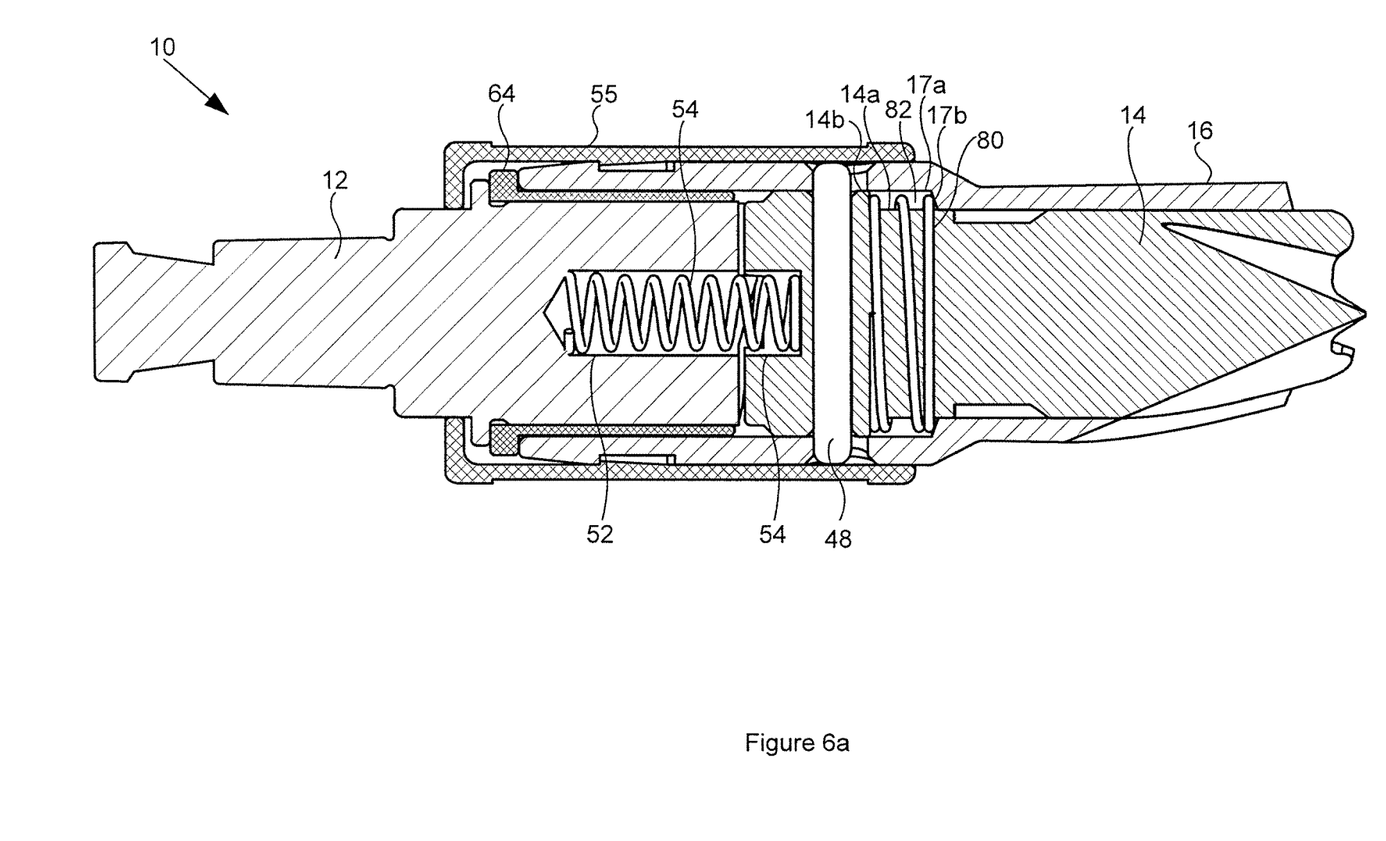
FIG. 6a is a cross sectional view of another preferred embodiment of the perforator according to the invention wherein the drill head is in its proximal position.
Figure 6B:
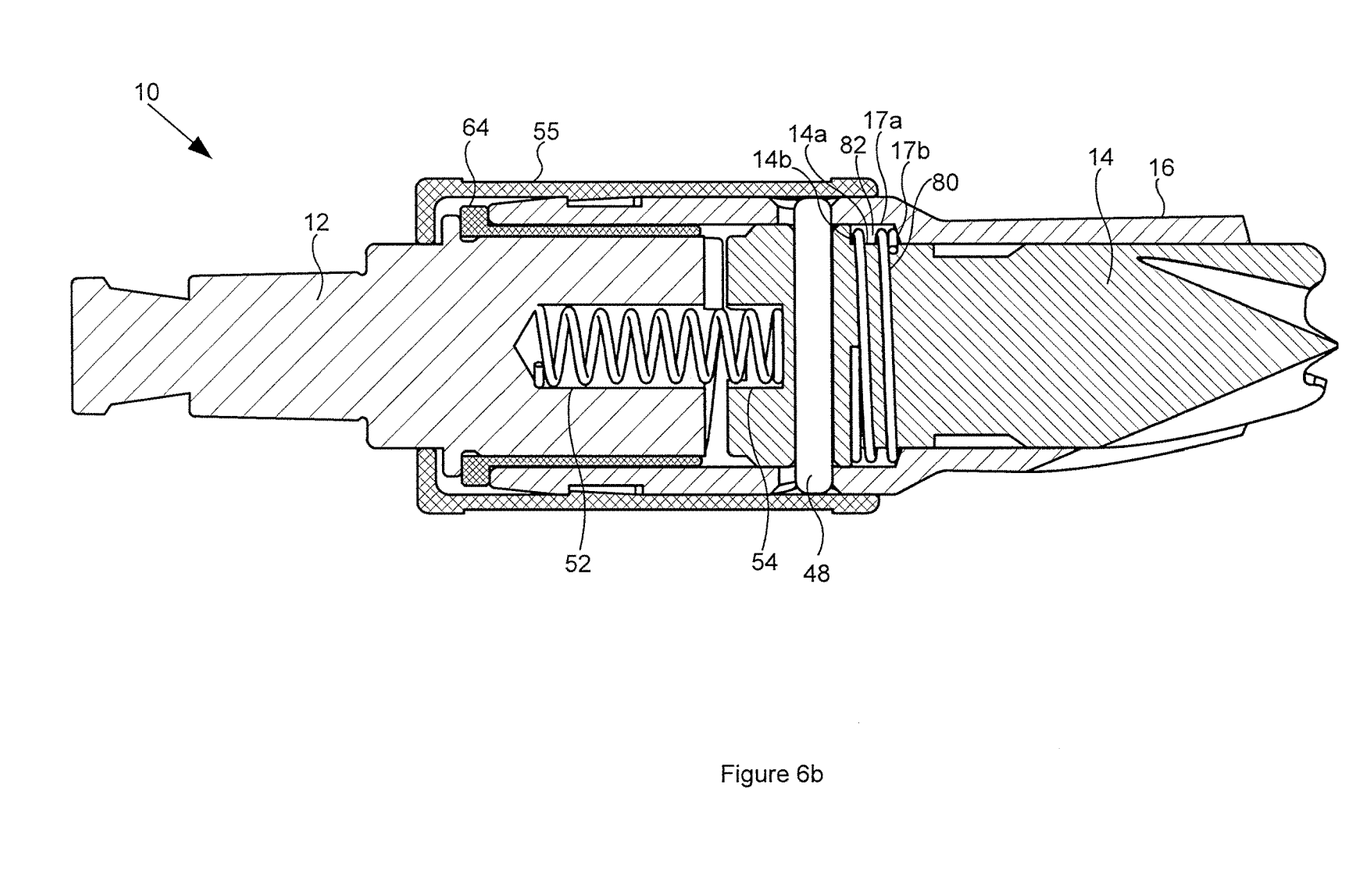
FIG. 6b is a cross sectional view of another preferred embodiment of the perforator according to the invention wherein the drill head is in its distal position.

Pulling back the drill head 14 can be further assisted by the application of a security spring 80 as illustrated in FIGS. 6a and 6b, which works with opposite effect as the spring 54 responsible for pushing out the drill head 14. the security ring 80 is arranged between an external wall 14a of the drill head 14 and an internal wall 17a of the chipping head 16, within a ring nest 82 defined by a proximal external circumferential flange 14b of the drill head 14 and a distal internal circumferential flange 17b of the chipping head 16. The length of the security spring 80 is determined from one direction by the position of the external circumferential flange 14b of the drill head 14 and from the other direction by the internal circumferential flange 17b of the chipping head 16. In the proximal position of the drill head 14, i.e. when the proximal end 18 of the drill head 14 abuts the distal end 22 of the drive shaft 12 and the first and second connection profiles 20, 24 engage with each other, the security spring 80 is slightly biased (compressed), as can be seen in FIG. 6a. The spring 54 and the security spring 80 are preferably dimensioned such that in the starting position illustrated in FIG. 6a, the resulting spring force is greater in the spring 54 arranged in the nest 52 of the drive shaft 12 and in the nest 50 of the drill head 14, than the spring force of the security spring 80. Preferably, such a spring 54 is used which has a greater spring constant than the spring constant of the security spring 80. It has been found by the inventor that an advantageous operation can be achieved by applying a spring 54 which has a spring constant that is 8-12 times greater, preferably approx. 10 times greater than the spring constant of the security spring 80. For example the spring 54 may have a spring constant of approx. 1.2 N/m while the security spring 80 may have a spring constant of approx. 0.14 N/m. The length of the spring 54 and the security spring 80 can be chosen for example such that the relaxed length of the spring 54 is approx. 1.5-2.5 times greater than the relaxed length of the security spring 80, preferably approx. 2 times greater, for example the relaxed length of the spring 54 may be approx. 20 cm, while the relaxed length of the security spring 80 may be approx. 10 cm.

In case the drill head 14 is distally displaced with respect to the chipping head 16 then the length 1 of the ring nest 82 decreases (see FIG. 6b), whereby the security spring 80 is compressed and the spring force exerted by it increases. The increased spring force acts in the proximal direction on the drill head 14 through its external circumferential flange 14b and presses the drill head 14 in the direction of its proximal position. At the same time the nest 52 of the drive shaft 12 and the nest 50 of the drill head 12 are displaced from each other by the same extent as the ring nest 82 is shortened. As a result the spring 54 therein is elongated, whereby the spring force exerted by it decreases, hence it exerts less pressure on the drill head 14 in the distal direction. Accordingly, the first spring 54 and the security spring 80 act in the opposite sense: in the proximal position of the drill head 14 the first spring 54 is more compressed, it exerts greater spring force which forces the drill head 14 in the distal direction, while the security ring 80 is less compressed, thus exerting a smaller spring force and forcing the drill head 14 in the proximal direction to a less extent. In the distal position of the drill head 14, however, the first spring 54 is less compressed, whereby the distal spring force decreases, while the security spring 80 becomes more compressed, thus the proximal spring force increases. Consequently, the spring 54 and the security spring 80 counterbalance each other's effect, which results in a more steady motion of the drill head 14, rendering the cutting motion more balanced. A further advantage of applying the spring 54 and the security spring 80 in combination is that a slight pressure drop due to either a temporary reduction of the pressing force exerted by the user or to a local change in the quality of the tissue, does not result in the disengagement of the drill head 14 and the drive shaft 12, since this pressure drop is compensated for by the security spring 80. However, in case the drill head 14 and the drive shaft 12 are disengaged, for example because the user interrupts the drilling operation, when the drilling is restarted the proximal spring force exerted by the security spring 80 helps to re-couple the drill head 14 and the drive shaft 12. It is also possible to achieve with the application of the security spring 80 that the disk 70c' created when drilling through the internal bone plate 70c does not become completely detached from the surrounding internal bone plate 70c, since the security spring 80 refrains the motion of the drill head 14 which is advancing in the distal direction during the above described decoupling process, and further helps to pull back the drill head 14, in this way the full penetration depth of the drill head 14 can be decreased and the dura tissue 70d can be better protected.

Various modifications to the above disclosed embodiments will be apparent to a person skilled in the art without departing from the scope of protection determined by the attached claims.

The invention claimed is:

1. A perforator for drilling bone tissue, comprising:
a drive shaft defining a first spring nest in the distal end thereof,
a drill head operably associated with the drive shaft, defining a second spring nest in the proximal end of the drive shaft, and
a chipping head arranged coaxially around the drill head, the drive shaft and the drill head having a common rotation axis, and the spring nests open into one another when the drill head and the drive shaft are engaged, and
wherein a first connecting profile is provided on a proximal end of the drill head, and a second connecting profile is provided on a distal end of the drive shaft and the drill head is arranged so as to be displaceable with respect to the chipping head along the rotation axis between a proximal position and a distal position, and in the proximal position the second connecting profile on the distal end of the drive shaft cooperates with the first connecting profile such as to transmit rotational motion from the drive shaft to the drill head, and in the distal position the first connecting profile on the proximal end of the drill head and the second connecting profile on the distal end of the drive shaft are disengaged, a first spring is arranged between the proximal end of the drill head and the distal end of the drive shaft, extends through the spring nests, and is compressed in the proximal position of the drill head; a ring nest is defined inside the perforator between an external wall and a proximal external circumferential flange of the drill head and an internal wall and a distal internal circumferential flange of the chipping head; and a security spring is arranged within the ring nest and is compressed in the distal position of the drill head.

2. The perforator according to claim 1, wherein a connection is provided between the drill head and the chipping head for transforming relative rotation of the drill head and the chipping head around the rotation axis into relative displacement along the rotation axis.

3. The perforator according to claim 2, wherein the drill head comprises a bore hole through an external surface of the drill head, and an inwardly opening groove with a proximal helical edge is provided in a wall of the chipping head, and the connection for transforming relative rotation of the drill head and the chipping head around the rotation axis into relative displacement is ensured by a bolt pin arranged in the bore hole of the drill head and extending into the groove of the chipping head, wherein the bolt pin is guided by the proximal helical edge.

4. The perforator according to claim 1, wherein the first connecting profile comprises at least one abutting surface, and the second connecting profile comprises at least one driving surface.

5. The perforator according to claim 4, wherein the at least one abutting surface and the at least one driving surface are rectangular.

6. The perforator according to claim 4, wherein the at least one abutting surface comprises at least two abutting surfaces that are formed rotation-symmetrically with respect to the rotation axis, each of the at least two abutting surfaces delimiting a projection projecting parallel with the rotation axis, and the at least one driving surface comprises a corresponding number of driving surfaces that are formed rotation-symmetrically with respect to the rotation axis, each of the corresponding number of driving surfaces delimiting a projection projecting parallel with the rotation axis, wherein the projection of each of the corresponding number of driving surfaces is formed with a wedge surface on a side opposite the driving surface, and a clearance is provided between the wedge surface and each of the corresponding driving surfaces for receiving the projections of the at least two abutting surfaces.

7. The perforator according to claim 4, wherein the at least one abutting surface comprises at least two abutting surfaces formed on projections, and the at least one driving surface comprises at least two driving surfaces formed on projections, and the at least two abutting surfaces and the at least two driving surfaces are arranged evenly spaced from each other around circumferences of two circles respectively.

8. The perforator according to claim 4, wherein the at least one abutting surface and the at least one driving surface each have a length of 0.4 to 1 mm, measured along the rotation axis.

9. The perforator according to claim 4, wherein the at least one abutting surface and the at least one driving surface each have a length of 0.6 to 0.9 mm, measured along the rotation axis.

10. The perforator according to claim 4, wherein the at least one abutting surface and the at least one driving surface each have a length of 0.7 mm, measured along the rotation axis.

11. The perforator according to claim 1, wherein a proximally extending wall of the chipping head extends beyond the drill head in the proximal direction and a slide ring is arranged between the drive shaft and the proximally extending wall.

12. The perforator according to claim 11, wherein the drive shaft and the chipping head are surrounded and interconnected by a cylindrical case, such that a proximal flange of the cylindrical case abuts a collar of the drive shaft, and an internal circumferential shoulder of the cylindrical case engages an external circumferential groove of the proximally extending wall of the chipping head.

* * * * *